United States Patent [19]
Gautsch

[11] Patent Number: 5,888,831
[45] Date of Patent: Mar. 30, 1999

[54] LIQUID-SAMPLE-SEPARATION LABORATORY DEVICE AND METHOD PARTICULARLY PERMITTING READY EXTRACTION BY SYRINGE OF THE SEPARATED LIQUID SAMPLE

[76] Inventor: James W. Gautsch, 451 S. Granados Ave, Solana Beach, Calif. 92075

[21] Appl. No.: 811,707

[22] Filed: Mar. 5, 1997

[51] Int. Cl.$^6$ .................................................... G01N 1/18
[52] U.S. Cl. ........................... 436/177; 422/72; 422/101; 422/102; 436/178
[58] Field of Search ..................................... 422/100, 102, 422/58, 61, 101, 104, 72; 436/174, 180, 177, 178, 810

[56] References Cited

U.S. PATENT DOCUMENTS

| | | | |
|---|---|---|---|
| 4,871,674 | 10/1989 | Matsui et al. | 422/102 |
| 4,953,741 | 9/1990 | Jessop et al. | 422/102 |
| 4,956,148 | 9/1990 | Grandone | 422/64 |
| 4,956,298 | 9/1990 | Diekmann | 422/102 |
| 5,352,413 | 10/1994 | Kratzer et al. | 422/100 |

*Primary Examiner*—Krisanne Thornton
*Attorney, Agent, or Firm*—Fuess & Davidenas

[57] ABSTRACT

In a plastic "miniprep" device for separating liquid samples including (i) a first, sample, cylindrical container having an inlet and an outlet opening between which a separation layer is arranged, the outlet opening typically being connected to and enclosed by an outlet spout, fitting within a cylindrical bore of (ii) a second, collecting, container receiving the separated liquid discharged from the outlet spout, the cylindrical first container is (a) of lesser diameter than is the bore, and (b) possessed of longitudinal exterior rib hat hold it eccentric within the bore. According to the (a) lessor diameter and (b) eccentric mounting, access may be had by hypodermic syringe or thin pipette down the side of the first container to separated liquid present at the bottom of the second container. Normally a large number of arrayed sample containers each positioned within a collection container are (i) loaded with samples, typically by use of a pipette, and then (ii) centrifuged in parallel while held in a rack, the (iii) separated liquid being withdrawn by syringe or pipette without necessity of separating the sample and collection containers, and (iv) the used containers discarded.

16 Claims, 1 Drawing Sheet

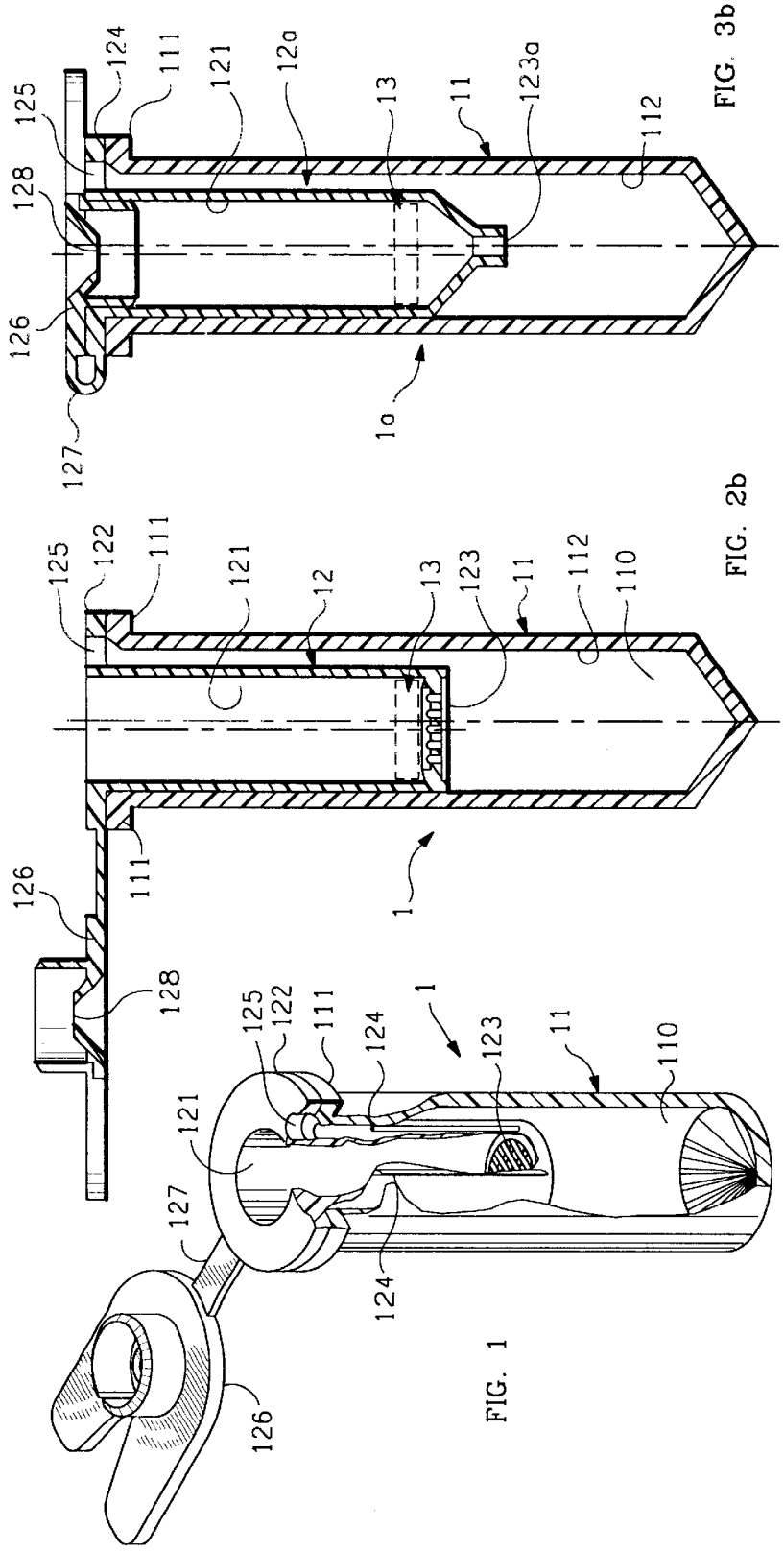

LIQUID-SAMPLE-SEPARATION LABORATORY DEVICE AND METHOD PARTICULARLY PERMITTING READY EXTRACTION BY SYRINGE OF THE SEPARATED LIQUID SAMPLE

BACKGROUND OF THE INVENTION

1. Field of the Invention

The present invention generally concerns laboratory devices and laboratory methods for separating liquid samples.

The present invention particularly concerns an improvement to a device for separating liquid samples including (i) a first, sample, cylindrical container having an inlet and an outlet opening between which a separation layer is arranged, the outlet opening typically being connected to and enclosed by an outlet spout, fitting within a cylindrical bore of (ii) a second, collecting, container receiving the separated liquid discharged from the outlet spout; the improvement being of the nature of making the cylindrical first container to be both (a) of lesser diameter than is the bore and (b) possessed of features, normally longitudinal exterior protuberances or ribs, that hold it eccentric within the bore, thus permitting that access may be made by hypodermic syringe down the side of the first container to a separated liquid present at the bottom of the second container.

2. Background of the Invention 2.1 General Laboratory Devices and Procedures for Separation of Liquid Samples The present invention will be seen to concern an improvement to an existing laboratory device commonly called a "miniprep", and to the laboratory procedures for the use of such a device.

A "miniprep" is concerned with the separation of liquid samples into their individual components, the extraction of particular components of a liquid sample, and/or the filtration of a liquid sample. The liquid sample can be, for example, a solution, a colloidal dispersion, or a suspension. The liquid sample is commonly only a few milliliters in volume.

The liquid sample is introduced—typically, for example, by pipette—into a first, sample, container of generally cylindrical form. The cylindrical sample container typically, but not necessarily, narrows to a spout at its lower region.

A separation layer normally in the form of filter paper, glass frit, a membrane, or other material with selective absorption properties is held in, and near the bottom of, the sample container. The liquid sample introduced into and held within the sample container penetrates this separation layer, flows through the spout, and enters into a second, collection, container that is arranged at a distance below the sample container.

The separation normally proceeds liquid drop by liquid drop, typically under (i) the centrifugal force of centrifuging or, else (ii) vacuum suction such as is described in U.S. Pat. No. 5,464,541 for a DEVICE AND METHOD FOR SEPARATING OF LIQUID SAMPLES as is further described below.

The present invention will be seen to concern improvements to "miniprep" containers that are generally centrifuged, and that are of a kind not normally used in vacuum separation (although it is not precluded that they should be so used).

The "miniprep" sample container and collecting container are generally of substantially tubular shape, typically holding but a few milliliters liquid each. (Ergo the "mini".) The separation layer normally abuts the bottom wall of the sample container, which bottom wall has the outlet opening formed therein. The outlet opening normally has a diameter of only a few tenths of a millimeter. The sample container normally fits (i) snugly, or nearly snugly in accordance with the showings of the aforementioned U.S. Pat. No. 5,464,541, and (ii) coaxially within the cylindrical bore of the cylindrical collection container.

The present invention will be seen to change this, and to be opposite in both its (i) fit and (ii) co-axial alignment.

Typically a large number of such sample containers are arranged side by side in rows and in columns, with the arrayed containers being interconnected by a support plate. The penetration of the separation layer in each and all of the sample containers is effected in parallel by force of (i) gravity, (ii) centrifuging, or (iii) vacuum. Each sample container must be withdrawn from its associated collection container after the separation process to expose the separated liquid collected in the bottom of the sample container. Contamination is possible if remaining liquid in the extracted sample containers drips onto other containers of the array, so this must be avoided. The exposed liquid contents in the collection containers are then typically removed with a syringe.

The present invention will be seen to make the laborious step or removing the sample containers from the collection containers unnecessary.

2.2 Specific Previous Patents Concerning Laboratory Devices and Procedures for Separation of Liquid Samples U.S. Pat. No. 5,464,541—issued Nov. 7, 1995 for a DEVICE AND A METHOD FOR SEPARATING LIQUID SAMPLES to James E. Aysta and assigned to Minnesota Mining and Manufacturing Company, St. Paul, Minn.—concerns a device for separating liquid samples. The device has a sample container the bottom wall of which has an outlet opening. The outlet opening is joined to an outlet spout extending in the axial direction of the sample container. A separation layer is on the bottom wall. A collecting container is arranged abutting and below the sample container. An exchange of air between the interior of the collecting chamber and the environment is possible, yet an escape of liquid is largely inhibited. The contact surface between collecting chamber and sample container, and the end of the outlet spout through which the liquid is discharged, are axially spaced apart. (This will be seen not be the case in the device of the present invention.)

In use a partial vacuum is pulled on the liquid sample. To this end a chamber that may be subjected to a partial vacuum is sealed in an airtight manner with a support plate that supports a number of sample containers. Within the chamber, there are collecting containers associated with each of the sample containers. The collecting containers are fitted into and supported in a rack. The liquid samples are pulled through the separation layer of each sample containers and into the associated collection container under force of the vacuum. Such an apparatus is used, for example, in medical laboratories for the simultaneous separating of a number of liquid samples.

Still earlier multi-well filtration devices have been disclosed in U.S. Pat. Nos. 4,777,021 and 4,427,415. Both reference devices have in common that liquid drops of samples penetrating separation layers will enter a common collecting vessel that is part of a vacuum chamber. The vacuum chamber is again sealed by a support plate interconnecting the individual sample containers arranged in a matrix-like manner. In the reference device for separating liquids, the sample components retained by, or in, the separation layer are of interest in the subsequent tests. The liquid penetrating the separation layer is "lost" for further analyzing purposes. It is frequently necessary for a chemical or bio-polymer separation of samples to individually and selectively catch the sample components that have penetrated the separation layer or have been washed out or removed from the separation layer by applying a solvent. This cannot be realized by using the reference devices.

U.S. Pat. No. 4,902,481 discloses a multi-well filtration apparatus for the assay of microliter quantities. The apparatus has a filter that is positioned in each well on a plate having an open spout positioned in the plate. The spout has a collar on its outer surface extending in a direction perpendicular to the vertical axis of the spout. The collar prevents a liquid droplet from climbing the outer surface of the spout from its open end.

In the '481 patent, the individual collecting containers are only a small distance apart. Due to the distance of the collecting containers to the sample containers, there is a risk that parts of a fluid drop to be received by a collecting container, arranged below a sample container, will enter a neighboring collecting container, thereby contaminating the filtrate thereof. Further, the forming of the drops may not be uniform in the device of U.S. Pat. No. 4,902,481. In particular, it is not uniform when the vacuum in the chamber is released for a short time in order to replace the set of collecting containers accommodated therein by a new one. When releasing the partial vacuum in the chamber, the lower surface of the plate can become wetted by the liquid drops. When a partial vacuum is subsequently generated, relatively large drops will form since sucked-in liquid expands along the lower surface because it is wetted. In this case, a drop may extend up to the annular collar, where it can be sucked off via the gap between the annular collar and the collecting container. Thus, the liquid does not get into the collecting container, but may possibly run into an adjacent collecting container (contamination) or flows along the outside of the respective collecting container.

Contamination of the liquid drops received by the collecting containers is particularly intolerable in the bio-polymer separation of liquid samples since, in this event, the examination of nucleic acids and proteins can be performed after a plurality (25 to 40) of self-replicating cycles, for example in a polymerase chain reaction (PCR), whereby even slight contaminations (contaminations of 1:1000) will be magnified and thus lead to erroneous results in the subsequent analysis.

SUMMARY OF THE INVENTION

The present invention contemplates typically small, typically disposable plastic, nested cylindrical containers for extracting through a filter certain fluid components of a liquid sample where, in particular, the separated fluid may readily be extracted by pipette or by syringe or the like from the nested containers without any necessity of disassembling the containers, thereby saving time and labor.

In accordance with the present invention, a cylindrical first, sample, container is located within the cylindrical bore of a cylindrical second, collection, container. However, the sample container is not concentrically so located within the collection container. Instead, the sample container (i) is of lesser diameter than is the bore of the collection container into which it is placed, and (ii) is held eccentrically displaced to one side of the bore. It is normally so held by a feature, preferably protuberances and more preferably elongate longitudinal ribs, that are preferably located upon its exterior surface. (The feature may alternatively be located near the rim of the sample container.) The sample container contains a filter.

In common terms, the sample container is lodged to one side within the bore of the collection container, leaving a void between itself and the interior wall of the collection container. This void—normally in the substantial shape of a prism having the cross-section of a crescent—is of importance to the present invention.

The sample container preferably has a pronounced rim that is, in accordance with the eccentric placement of the sample container within the bore of the collection container, also eccentric. This rim is sufficient to, nonetheless to the eccentric placement of the sample container within the bore of the collection container, substantially overlay the top opening of the bore of the collection container in regions outside the sample container. An opening, normally in the form of a minute hole, that is sufficient to accept the needle of a syringe is placed in the rim of the sample container at a position outside its bore and outside its wall, and over the void that is between the sample container and the collection container.

The sample container further preferably has a top lid. This lid is preferably hinged to the rim of the sample container, more preferably by a live hinge. The lid covers the open top of the sample container and, preferably also, its rim. This means that when the sample container is (eccentrically) located within the bore of the collection container, then the open top of the collection container is covered in part by both (i) the rim, and (ii) the lid, of the sample container.

The lid preferably has and defines two voids, or, more preferably, one void in the form of an orifice and one void in the form of a relieved region. The orifice is central to the bore of the sample container (which is concentrically displaced within the bore of the collection container). It is preferably conical in shape. Meanwhile, the relieved area is preferably in the shape of the letter "V" with the minute hole of the sample container's rim being at the apex of the "V" when the lid is closed.

The use of each and all of (i) the hole within the sample container's rim, aligned with (ii) the "V"-shaped relieved area of the lid, (iii) the conically-shaped orifice within the lid, is as follows. A tip of a pipette, or a needle of a hypodermic syringe, or the like is guided by the conically-shaped orifice of the lid into the central reservoir of the sample container. A tip or needle is so inserted so as to, for example, load a liquid sample into the sample container above the filter. The loaded sample container is held (eccentrically) nested within the collection container.

Both nested containers are, typically, centrifuged. Fluid drawn through the filter, called "separated fluid", is collected at the bottom of the collection container.

Importantly, a tip of a pipette, or the needle of a hypodermic syringe or the like may now be guided by (i) the lid's "V" into (ii) the rim's minute hole, The pipette tip, or syringe needle, proceeds down the crescent-shaped prismatic cavity between the sample container and the collection container until ultimately reaching the separated liquid at the base of the collection container. This liquid is then "sucked up" and withdrawn.

The retrieval of the separated liquid for subsequent laboratory purposes is accordingly much facilitated because the nested containers need not be separated, as was heretofore the case. Contamination of the separated liquid is avoided.

The present invention may also be considered to be embodied in a method of separating a liquid sample. In the method a liquid sample is entered with a pipette or the like into a central reservoir of a first cylindrical, sample, container. This sample container has (i) both an inlet and an outlet opening, (ii) a separation layer located between the inlet and the outlet opening, and (iii) predetermined exterior features, normally in the form of at least one protuberance, that serve to regionally increase the diameter of the sample container.

The first, sample, container is placed within the cylindrical bore of a larger, second, collection container. In accordance with its exterior features (normally the exterior protuberance (s)), the sample container becomes lodged eccentrically within the bore.

The liquid sample within the sample container, which is in turn within the collection container, is centrifuged. A separated fluid collects within a reservoir at the bottom of the collection container.

This separated fluid is then withdrawn from the collection container—without removing the sample container from its bore—by inserting the tip of a pipette, or a needle of a syringe or other extraction device, though the void located between the interior of the collection container and the exterior of the sample container until the needle contacts the separated fluid within the reservoir.

Both the initial loading of the liquid sample into the central reservoir, and the later withdrawal of the separated fluid from the reservoir of the collection container, may each be suitably abetted by guide features on a lid to the sample container.

These and still other aspects and attributes of the present invention will become increasingly clear upon reference to the following drawings and accompanying specification.

BRIEF DESCRIPTION OF THE DRAWINGS

FIG. 1 is a perspective view of first variant embodiments of each of two—a sample and a collection—containers of the present invention nested together, the hinged lid of the inner, sample, container being shown open.

FIG. 2a is a cut-away top plan view, and FIG. 2b is a side plan view taken along aspect line 2b—2b shown in FIG. 2a, of the first variant embodiments of each of the two, sample and collection, containers of the present invention nested together previously seen in FIG. 1, the lid of the inner, sample, container still being shown open.

FIG. 3a is a cut-away top plan view, and FIG. 3b is a side plan view taken along aspect line 3b—3b shown in FIG. 3a, of an alternative, second, variant embodiment of the sample container nested within the first embodiment of the collection container—similarly to the embodiments previously shown in FIGS. 1 and 2—with the lid of the inner, sample, container now being shown closed.

DESCRIPTION OF THE PREFERRED EMBODIMENTS

Preferred embodiments of a liquid separation device 1, 1a according to the present invention are shown in perspective view in FIG. 1, in top plan views in FIGS. 2a and 3a, and in cut-away side plan views in FIGS. 2b and 3b. Second embodiment device 1a best seen in FIG. 3b is only very slightly different from the first embodiment device 1 in that the inner, sample, container 12a has and presents a spout 123a (illustrated in FIG. 3b) instead of a sieve surface 123 that (illustrated in FIG. 2b).

The devices 1, 1a of the invention are useful for the separation of liquid samples into their individual components, for the extraction of particular components of a liquid sample, and/or for the filtration of a liquid sample. The liquid sample can be, for example, a solution, a colloidal dispersion, or a suspension. The liquid sample is commonly only a few milliliters. Accordingly, the preferred devices 1, 1a as are shown in the Figures are small, being typically only about one an one-half inches (1 ½") in overall length by seven-sixteenth inch (⁷⁄₁₆") in major diameter.

Considering the Figures, the depicted first embodiment of a first, collection, container 11 is a common vial. It may readily be commercially procured in great quantities, for example as part number 05-407-25A from Fisher Scientific Company of 711 Forbes Avenue, Pittsburgh, Pennsylvania 15219-4785, USA. It is commonly inexpensively made from polypropylene plastic, as is the more complex sample container 1. The collection container 11 defines and interior reservoir 110, and an upper rim 111. As may well be understood, the collection container 11 can be procured in other embodiments differing in length and volume, square versus tapered tips, opacity, etc., etc.

Because the collection container 11 is a standard, commodity, item, the present invention may be seen to most strongly reside in a second, sample, container 12, 12a. This is indeed the case, and the preferred structure of this sample container 12, 12a is quite sophisticated.

Each sample container 12, 12a is removably nested in a collection container 11 so as to have a modest,finger-tight, friction fit. It is typically delivered into service already so nested and will often never be removed during (i) use and/or (ii) subsequent disposal.

Each sample container 12, 12a contains a filter 13, illustrated in phantom line for being but an optional part of the present invention. The filter 13, may, or may not, be delivered into service already into the sample container 12, 12a depending upon the requirements of the user. The filter 13 is commonly in the shape of a disk co-extensive in area with the interior cylindrical bore 121 of the sample containers 12, 12a. It also typically has a modest friction fit once inserted. The filter may be, for example stamped in great quantity form the part no. X4911 sheet filter material of Dorex technologies, 500 Bohannon Road, Fairburn Ga., 30213, USA. The filter 13 is optionally delivered into service already installed within the sample containers 12, 12a. It also is often never removed during its use and subsequent disposal.

The rim 111 of the upper opening of the collection container 11 abuts a rim 122 of the sample containers 12, 12a. The seal presented thereby is typically not airtight. As will be seen, holes and orifices permit gas communication to and between the interior reservoirs of the sample container 12, 12a and the collection container 11, in any case.

The sample container 12 (shown in FIG. 2b) has a sieve 123 as its lower surface. The sample container 12a (shown in FIG. 3b) has a spout 123a as its lower surface. Each nested sample container 12, 12a clearly projects into the collection container 11 through a top opening of the same. Even with the spout 123a (of the sample container 12a), the point of any liquid (drop) discharge from the bottom of the sample containers 12, 12a and the contact surface of the collection container 11 do not lie in the same horizontal plane, but are spaced apart vertically. This distance is such that any drop formed at the bottom of the sample containers 12, 12a will not contact the receiving surface of the collection container 11.

In that preferred embodiment of the device 1 of the present invention using the second embodiment sample container 12a (shown in FIG. 3b), the outlet spout 123a surrounding the outlet opening projects fairly deeply into the collection container 11. The inner diameter of the outlet spout 123a is 0.1 to 1 mm, preferably about 0.5 mm. The length of the outlet spout 123a, measured from the lower surface of the bottom wall, is 5 to 20 mm, preferably about 6 mm. Thus, the relation between the inner diameter and the length of the outlet spout 123a lays within the range from 0.005 to 0.2 mm, preferably at about 0.08 mm. On all sides around its end (point of liquid or drop discharge), the outlet spout 123a is shielded from the adjacent collection containers by the walls of the individually associated collection container 11. Thereby, cross-container contamination is practically excluded.

A further protection is provided by the contact between the collection container 11 and the sample container 12 in the area of the opening of the former. However, this contact is commonly not, and need not be, airtight. When liquid from a sample inserted into the sample container 11 is pressed through the filter 13 by centrifuge, then the separated fluid entering the collection container 11 would cause a rise in the pressure within the collection container 11 were the same sealed in an airtight manner. Therefore, the sealing of the collection container is not air-tight.

The cylindrical sample containers 12, 12a are each shown located within a cylindrical bore 112 of an associated cylindrical collection container 11. However, and importantly, the sample containers 12, 12a are not concentrically so located. Instead, each sample container 12, 12a is of lesser diameter than is the bore 112 of the collection container 11 into which it is placed. Moreover, each sample container 12, 12a is held eccentrically displaced to one side of the bore 112. It is normally so held by special exterior features. These features may be associated with the rim 121 (yet to be discussed) of the sample containers 12, 12a, but the features are preferably in the form of protuberances, and more preferably elongate longitudinal ribs 124 (best seen in FIG. 1b), that are located upon its exterior surface.

It should be understood the eccentric location is, in accordance with the present invention, accomplishable by other features than simply the preferred ribs. Protuberances might be, for example, in the form of buttons or knobs or mounds, etc. Moreover, protuberances on the external cylindrical surface of the sample container 12, 12a need not be used at all! Instead, it is sufficient to make an eccentric collar at the region of the rim 124 which collar (not shown) will suffice to hold the sample container 12 eccentric within the bore of the collection container 11.

By action of its locating features of any nature, each sample container 12, 12a is accordingly lodged to one side within the bore 112 of the collection container 11, as illustrated. A void is left between the exterior of the sample containers 12, 12a and the interior wall of the associated collection container 11. This void is in the substantial shape of a prism having the cross-section of the crescent, as is best observed in dashed-line outline in FIG. 2a.

As is also best observed in FIG. 2a, the rim 122 of the sample containers 12, 12a is, in accordance with the eccentric placement of each sample container 12, 12a within the bore 112 of the associated collection container 11, also eccentric. This rim 122 is sufficient to, nonetheless to the eccentric placement of each sample containers 12, 12a within the bore 112 of an associated collection container 11, substantially overlay the top opening of the collection container 11 in the region outside the sample containers 12, 12a. This is best observed in FIGS. 3a and 3b.

A minute hole 125, sufficient to accept the needle of a syringe, is placed in the rim 122 at a position over the void between the sample container 12, 12a and the collection container 11.

Each sample container 12, 12a preferably has a lid 126. The lid 126 is preferably hinged, more preferably by the illustrated live hinge 127. The lid 126 may be pivoted on its hinge 127 from the open position shown in FIGS. 2a, 2b to the closed position shown in FIGS. 3a, 3b.

The lid 126 covers the open top of the sample container 12, 12a and, preferably also, its rim 122. This means that when the sample container 12, 12a is (eccentrically) located within the bore 112 of the collection container 11, the open top of the collection container 11 is covered in part by both (i) the rim 122, and (ii) the lid 126, of the sample container 12, 12a.

The lid 126 preferably has and defines two voids. One void is preferably in the shape and form of the orifice 128. The other void is preferably in the shape and form of the relieved region 129 (best seen in FIG. 3a). The orifice 128 is central to the cavity of the sample container 12 (which sample container 12, 12a is concentrically displaced within the bore 112 of the collection container 11). It is preferably conical in shape, as best illustrated in FIGS. 2b and 3b. Meanwhile, the relieved area 129 is preferably in the shape of the letter "V", as is best illustrated in FIGS. 2a and 3a. The minute hole 125 within the rim 124 of each sample container 12, 12a is located at the apex of the"V".

The overall alignments are such that the hole 125 within the rim 122 of each sample container 12, 12a is aligned with the "V"-shaped relieved area 129 of the lid 126. Meanwhile, the conically-shaped orifice 128 within the lid 126 is aligned with the central reservoir of the sample container 12, 12a, as previously explained.

The use of the entire device 1 is as follows. A tip of a pipette, or a needle of a hypodermic syringe, or the like (not shown) is guided by the conically-shaped orifice 128 of the lid 126 (of the sample container 12, 12a) into the central reservoir of the sample container 12a, 12b. A tip or needle is so inserted to, for example, load a liquid sample into the sample container 12, 12a above the filter 13. The loaded sample container 12, 12a is held (eccentrically) nested within the collection container 11.

Both nested containers 11, 12 (12a) are then typically centrifuged. Separated fluid drawn through the filter 13 is collected at the bottom of the collection container 11. The tip of a pipette, or the needle of a hypodermic syringe, or the like (again not shown) is now guided by the "V"-shaped relieved area 129 of the lid 126 into the minute hole 125 of the rim 122. The tip, or needle, proceeds down the crescent-shaped prismatic cavity between the sample container 12, 12a and the collection container 11 to reach the separated liquid at the base of the collection container 11. This liquid is then "sucked up" and withdrawn.

The sample container 12 and its lid 126 are advantageously formed integrally. The sample container 12a and its outlet spout 123a and its lid 126 are also advantageously formed integrally. The sample containers 12, 12a as well as the collection container 11 are preferably provided as plastic parts, preferably molded. A great number of sample containers 12, 12a nested in collection containers 11 are commonly arrayed and held on a common support plate (so-called micro-titer plate).

The device 1 of the invention is particularly suited for implementation in an apparatus in which a plurality of sample containers are arranged closely adjacent to each other so that a simultaneous separation of a plurality of liquid samples is made possible. The nested containers are arranged, for example, side by side in a single row and interconnected (via a sample container strip), or they can be arranged in rows and columns in a two-dimensional matrix and interconnected, the columns being orthogonal in respect of the rows. In any case, each sample container 12, 12a is individually associated with a collection container 11. Adjacent sample containers 12, 12a do not have to be appreciably spaced apart one to the next in order to prevent contamination among and between the arrayed collection containers 11. A high packing density of arrayed nested containers is supported. As is known from conventional microfilter plates, some 96 sample containers may typically be accommodated in an area of about 100 cm.$^2$. The length dimensions of a standard micro-titer plate are about 12.3 cm by 8.2 cm.

With the device 1 of the present invention, it is possible to perform a physical separation, a chemical separation, or a bio-polymer separation or extraction of liquids containing plant, animal or human cells. The device 1 permits, in particular, the separation of nucleic acids and/or proteins of the cells. To this effect, the liquid in the sample container 12, 12a penetrates the filer 13, commonly of selectively adsorbing material. The filtered liquid, called separated fluid, exiting the filter 13 flows or drips from the bottom of the sample container 12, 12a and enters the collection container.

Preferably, the layer of selectively adsorbing filter material has chromatographic properties, which can include ion exchange properties or affinity-chromatographic properties if the layer comprises suitable affinity ligands. A preferred filter separation layer comprises a fibrillated polytetrafluoroethylene matrix having enmeshed therein sorptive derivatized silica particulate as are disclosed in U.S. Pat. Nos. 4,810,381 and 4,699,717, respectively.

Subsequent to filtration, the collection container 11 may be f Ad replaced by another one, and a liquid containing a solvent may be applied to the filter 13. This serves to selectively remove a certain portion of the material adsorbed in the filter so that it may enter the collection container 11.

It is essential that this removed material should be captured free of any contamination, the uncontaminated condition being ensured even when a large number of nested containers spaced closely side by side are used. Such replacement of the collecting containers is particularly necessary in bio-polymer separations, since respectively different materials adsorbed in the filter layer have to be removed and collected several times by applying different liquids containing different solvents.

As is appreciated by those skilled in the art, variation in drop characteristics can be due to wetting of the underside of the bottom of the sample container 12, 12a. In the device 1 of the present invention, the drop inlet point is shifted farther into the collection container 11 in proportion to the length of the outlet spout 123a. This eliminates adverse influences on drop characteristics.

The separation filter layer 13 of the device 1 of the present invention may comprise one or several layers. Preferred separation layers comprise a fibrillated polytetrafluoroethylene matrix having sorptive particulate enmeshed therein, as is disclosed, for example, in U.S. Pat. No. 4,810,381. In one embodiment, the separation layer may be formed by two porous fixation means, in particular frits, with particles therebetween. Preferably, the particles can be in the form of bulk material, have chromatographic properties as described before. The preferred particles are made from a material that is based on silica gel, dextran or agarose. Frits may consist of glass, polyethylene (PE) or polytetrafluoroethylene (PTFE) and have a pore size of about 0.1–250 mu.m, preferably about 100 mu.m. The thickness of the particle layer is about 1–10 mm, preferably 2.5 mm, with a particle size of 1–300 mu.m, preferably 16–23 mu.m.

According to a further advantageous configuration and use of the device 1 of the present invention, the separation filter layer 13 may incorporate a support membrane in which the adsorptive particles are embedded. Since this support membrane tends to be rather weak, presenting a possibility that it can burst, a back-up fabric or fibrous layer can be arranged below the support membrane in order to provide integrity to the support membrane on the bottom wall of the sample container 12, 12a. Such a support membrane preferably consists of a non-woven polyalkylene fibrous material such as polypropylene or polyethylene.

The device 1 of the present invention is not limited to any particular dimensions. Generally, the device 1 of the invention can be produced in any desired size. Even the described embodiment of the invention for simultaneously separating a plurality of samples is only exemplary, and is not limited to any particular dimensions. However, for the sake of completeness, nominal numeric specifications of the preferred embodiment of the device 1 are as follows:

By reference to FIGS. 1 and 2, the device 1 clearly has a tubular sample container 12 the upper end which is open and defines an inlet opening. This inlet opening commonly extends over the entire upper face of the tubular sample container 12. Meanwhile, the lower face has a circular bottom wall. The bottom wall has a central outlet opening provided therein. This outlet has a diameter of a few $\frac{1}{10}$ mm (0.2 to 0.9 mm, preferably 0.4 to 0.6 mm). The lower surface of bottom wall may also, in the sample container 12a, have the conical outlet spout 123a formed thereon. This spout 123a encloses the outlet opening and extends in the axial direction of sample container 12a. This outlet spout 123a preferably tapers towards its free end, commonly having a length of up to 2 cm, preferably 0.1 to 1.0 cm and more preferably 0.2 to 1.0 cm. The diameter, optionally decreasing towards the end, is typically 0.3 to 2.0 mm.

Within the sample containers 12, 12a there is a separation filter layer 13 of selectively adsorbing material. The filer layer 13 is commonly made of a membrane with adsorption properties. This filter layer 13 is disposed on the bottom wall of the sample container 12, 12a, and covers its outlet opening. A optional rubbery, preferably plastic, retaining ring (not shown) may serve to pressing against the inner wall of sample container 12, 12a so as to keep the filter layer 13 set tight against the bottom wall. Normally no such "retaining ring" is necessary.

The filer layer 13 permits selective adsorption, in particular, of nucleic acids and proteins from liquids containing complete plant, animal or human cells or parts thereof.

The collection container 11 is also preferably tubular in shape, and is commonly formed like a test tube. The bottom portion of the collection container 11 may also be conically tapered downward, as illustrated. However, it may also be square. In accordance with the present invention, the exterior diameter of the sample container 12 is less than the interior diameter of the collection container 11, typically 8 mm. versus 9 mm. The collection container 11 is preferably has about 1 ½ times the axial length of the sample containers 12, 12a.

The upper end of the collection container 11 is open; this open end forms the opening of collection container 11 that receives the sample container 11. The rim 111 of the collection container 11 abuts the rim 122 of the sample container 12. Each rim defines an major opening to its associated container. The contact of the two rims 111, 122 does not form an airtight seal. Rather, an exchange of air between the interior of collection container 11, in particular, and the environment is possible.

As can be seen in FIG. 3b, an outlet spout 123a of the sample container 12a projects a bit, i.e., a few millimeters up to a few centimeters, into the collection container 12. The spout 123a preferably projects downward by more than 2 mm, having a length of 6 mm or more. The sample containers 12, 12a and the collection container 11 respectively have outer diameters of about 8 mm. and 10 mm.

Given these dimensions, one may arrange 96 nested containers spaced apart at a distance of about 1 mm in a matrix-like manner on a common support plate of microtiter plate standard.

In use of the device 1 of the present invention, the retrieval of the separated liquid for subsequent laboratory purposes is much facilitated because the nested containers need not be separated, as was heretofore the case. Contamination of the separated liquid is avoided. Furthermore, contamination of the liquid received by the collecting container is avoided, even in tightly packed arrays.

In accordance with the preceding explanation, variations and adaptations of the liquid separation device in accordance with the present invention will suggest themselves to a practitioner of the fluid and mechanical engineering and design arts.

In accordance with these and other possible variations and adaptations of the present invention, the scope of the invention should be determined in accordance with the following claims, only, and not solely in accordance with that embodiment within which the invention has been taught.

What is claimed is:

1. A device for separating liquid samples comprising:
   a first, sample, cylindrical container, defining an interior reservoir having an inlet and an outlet opening, of a predetermined exterior diameter that is regionally increased by an exterior feature;
   a second, collection, container defining an interior reservoir having a cylindrical bore in which fits the sample container eccentrically in accordance with the exterior feature of the sample container;
   wherein the collection container receives in its reservoir separated liquid discharged from the reservoir of the sample container through the sample container's outlet opening;
   wherein, by the eccentric location of the sample container within the bore of the collection container, a void is created between the inside of the collection container and the outside of the sample container through which void access may be had by a needle of a syringe to the separated liquid within the reservoir of the collection container; and
   a lid to both the collection container and the sample container, the lid having and defining (1a) a first hole, sufficient to accept the needle of a syringe, in position over the reservoir of the sample container and (1b) a first exterior feature helping to guide a needle of a syringe into the first hole and into the sample container's reservoir, and (2a) a second hole, sufficient to accept the needle of a syringe, in position over the void and (2b) a second exterior feature helping to guide a needle of a syringe into the void and into the reservoir of the collection container.

2. The device for separating liquid samples according to claim 1 wherein the exterior feature of the sample container comprises:
   at least one protuberance upon an exterior surface of the sample container.

3. The device for separating liquid samples according to claim 2 wherein the at least one protuberance of the sample container comprises:
   two spaced-parallel longitudinal ribs upon the exterior surface of the sample container.

4. The device for separating liquid samples according to claim 1
   wherein the outlet opening of the first, sample, cylindrical container, terminates in a spout.

5. The device for separating liquid samples according to claim 1
   wherein the cylindrical collection container has and defines a rim at the top of its bore; and
   wherein the cylindrical sample container has and defines a rim, eccentric to its central axis, that,substantially overlies the rim of the collection container when the sample container is eccentrically lodged within the bore of the collection container.

6. The device for separating liquid samples according to claim 5
   wherein the sample container's rim has and defines a hole, sufficient to accept the needle of the syringe, in position over the void.

7. The device for separating liquid samples according to claim 1 wherein the lid of the sample container comprises:
   a hinge to the sample container.

8. The device for separating liquid samples according to claim 7 wherein the hinge comprises:
   a live hinge that is integral with the sample container.

9. The device for separating liquid samples according to claim 1 wherein the lid's first hole comprises:
   a circular orifice.

10. The device for separating liquid samples according to claim 9 wherein the lid's first feature comprises:
    a conical surface to the circular orifice so as to help guide the needle of the syringe into the central reservoir of the sample container.

11. The device for separating liquid samples according to claim 1 wherein the lid's second feature comprises:
    a relieved area in the lid.

12. The device for separating liquid samples according to claim 11 wherein the relieved area in the lid of the sample container is in the substantial shape of a "V" with the second hole in the lid located at the apex of the "V", therein so as to help guide the needle of the syringe into the void.

13. The device for separating liquid samples according to claim 1 further comprising:
    a separation layer located between the inlet and the outlet opening of the sample container.

14. A device for separating liquid samples comprising:
    a first, sample, cylindrical container, having and defining (i) an interior reservoir with an inlet and an outlet opening, with a predetermined exterior diameter that is regionally increased by (ii) at least one protuberance, and (iii) a hinged lid having and defining (1a) a first hole, sufficient to accept the needle of a syringe, in position over the reservoir of the cylindrical container and (1b) a first guidance feature helping to guide a needle of a syringe into the first hole and into the cylindrical container's reservoir, and (2a) a second hole, and (2b) a second guidance feature, both in position beyond to the exterior diameter of the cylindrical container respectively for accepting and for guiding the needle of a syringe;

a separation layer located between the inlet and the outlet opening of the sample container;

a second, collection, container having a cylindrical bore in which fits the sample container eccentrically in accordance with the at least one protuberance of the sample container;

wherein the collection container receives in its reservoir separated liquid discharged from the sample container;

wherein, by the eccentric location of the sample container within the bore of the collection container, access may be had by a needle of a syringe down through the (2a) second hole as guided by the (2b) second guidance feature into a void located between the inside of the collection container and the outside of the sample container to the separated liquid within the reservoir of the collection container.

15. A sample container for use with a stock cylindrical collection container in the separation of liquid samples, the sample container comprising:

a cylindrical body, defining an interior reservoir and having an inlet and an outlet opening, of a predetermined exterior diameter that is regionally increased by at least one protuberance; and wherein the cylindrical body regionally increased in exterior diameter by the at least one protuberance (i) fits snugly within a cylindrical bore of the collection container, and (ii) eccentrically so fits within the cylindrical bore thus leaving a void between the outside of the body and the interior of the collection container; and a lid to the body, the lid having and defining (1a) a first hole, sufficient to accept the needle of a syringe, in position over the reservoir of the body and (1b) a first exterior feature helping to guide a needle of a syringe into the first hole and into the body's reservoir, and (2a) a second hole, sufficient to accept the needle of a syringe, which falls in position over the void when the body is fit eccentrically snugly within the collection container, and (2b) a second exterior feature then helping to guide a needle of a syringe into the void and into a reservoir of the collection container;

wherein, by action of the eccentric location of the sample container within the bore of the collection container and the lid, guided access may interchangeably be had by a needle of a syringe either through the second hole and down the void that is located between the inside of the collection container and the outside of the to the separated liquid within the reservoir of the collection container or else through the first hole into the reservoir of the body.

16. A method of separating a liquid sample comprising:

entering with a pipette a liquid sample into a central reservoir of a first cylindrical, sample, container having (i) an inlet and an outlet opening, (ii) a separation layer located between the inlet and the outlet opening, (iii) a predetermined exterior diameter that is regionally increased by at least one protuberance and (v) a lid; while guiding the entering of the liquid sample into the sample container with the pipette by a feature in the lid to the sample container;

placing the first, sample, container within a cylindrical bore of a larger, second, collection container so that the sample container is lodged eccentrically within the bore in accordance with its at least one exterior protuberance;

centrifuging the liquid sample within the sample container within the collection container so that separated liquid collects within a reservoir at the bottom of the collection container; and withdrawing the separated liquid from the collection container without removing the sample container from its bore by inserting a needle of an extraction device though a void between the interior of the collection container and the exterior of the sample container eccentrically mounted within the bore until the needle contacts the reservoir; while guiding the withdrawing of the separated liquid from the collection container with the pipette by another feature in the lid to the sample container.

* * * * *